Figure 1:
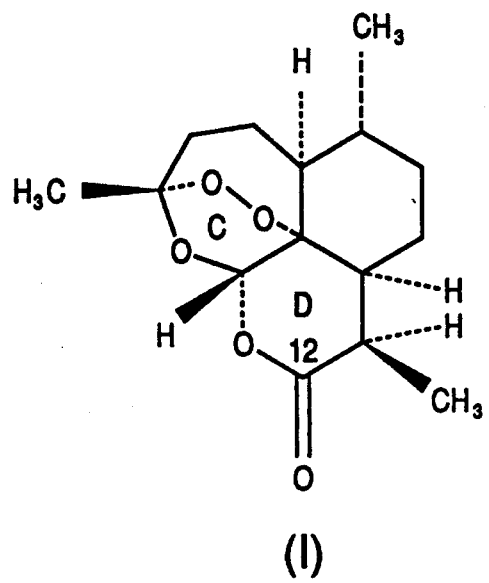

United States Patent [19]

Buchs et al.

[11] Patent Number: 5,011,951

[45] Date of Patent: Apr. 30, 1991

[54] SYNTHESIS OF ARTEMISININELACTOL DERIVATIVES

[75] Inventors: Peter Buchs, Bioggio, Switzerland; Arnold Brossi, Bethesda, Md.

[73] Assignee: World Health Organization, Switzerland, Switzerland

[21] Appl. No.: 316,282

[22] Filed: Feb. 27, 1989

[30] Foreign Application Priority Data

Feb. 25, 1988 [GB] United Kingdom ................. 8804372

[51] Int. Cl.$^5$ .......................................... C07D 321/02
[52] U.S. Cl. .................................................. 549/348
[58] Field of Search ........................................ 549/348

[56] References Cited

PUBLICATIONS

The Merck Index, 10th edition, Publ. Merck & Co., Rahway, N.J.; U.S.A. p. APP-3 (1983).

Primary Examiner—Nicky Chan

[57] ABSTRACT

A process for the epimerization of α- to β-ethyletherartemisininelactol (arteether) or preparation of arteether, useful in the treatment of malaria, from artemisininelactol, comprises reacting starting material in a solvent including an acid catalyst, the reaction of artemisininelactol also including an etherifying ethyl moiety, and isolating the product.

6 Claims, 1 Drawing Sheet (I)

β-series (II) R = OH (III) R = OCH$_2$CH$_3$

α-series (II) R = OH (IV) R = OCH$_2$CH$_3$

SYNTHESIS OF ARTEMISININELACTOL DERIVATIVES

This invention relates to the synthesis of derivatives of dihydroqinghaosu (artemisininelactol) useful for the treatment of malaria.

Dihydroqinghaosu (DQHS) is a compound of formula (II) in the accompanying drawing and is a cyclic hemiacetal which behaves in solution as a mixture of the $\alpha$ and $\beta$ anomers. DQHS is a derivative of qinghaosu (QHS) (artemisinine), shown in the accompanying drawings as formula (I), which is a sesquiterpene peroxide and the active ingredient of *Artemisia annua L.*, extracts of which have been used as an antimalarial preparation in the Republic of China for centuries. QHS is, however, only sparingly soluble in water or oils and is not well absorbed by the gastrointestinal tract. There have therefore been attempts to provide more potent analogues of QHS with improved bioavailability.

DQHS is formed from QHS by reduction with sodium borohydride in methanol to give the product in crystalline form. The anomer composition varies from batch to batch, resulting in compounds with different melting points and optical rotations. Derivatives of $\alpha$ and $\beta$ DQHS which have hitherto been prepared include the methyl ether derivative of $\beta$-DQHS and the sodium salt of a hemisuccinate of $\alpha$-DQHS, both of which showed improved properties. However, the latter compound, although being highly effective against malaria in animal models, proved to be extremely sensitive to hydrolysis, rendering unclear whether the active species was the hemisuccinate itself or its hydrolysis product. The former compound, on the other hand, was found to be much more stable than and similar in antimalarial activity to the hemisuccinate when administered as an intramuscular injection as an oily solution.

A further derivative of DQHS is the ethyl ether derivative which, in the $\beta$ form (III), is a stable crystalline solid. It is at least as active as the methyl ether derivative of $\beta$-DQHS and is more lipophilic, which renders it more readily accumulatable in brain tissue and, therefore, potentially more potent against cerebral malaria. The ethyl ether derivative of $\beta$-DQHS is known as arteether. However, the preparation of arteether as known hitherto requires the use of toxic solvents such as benzene, is not suitable for commercial-scale production and yields the product contaminated with approximately 25% of its inactive $\alpha$-epimer.

It is an object of the present invention to provide a process for the synthesis of arteether and in particular the conversion of the ethyl ether derivative of DQHS to arteether.

FIG. 1 provides a representation of the structure of qinghaosu (formula I)

Figure 2:
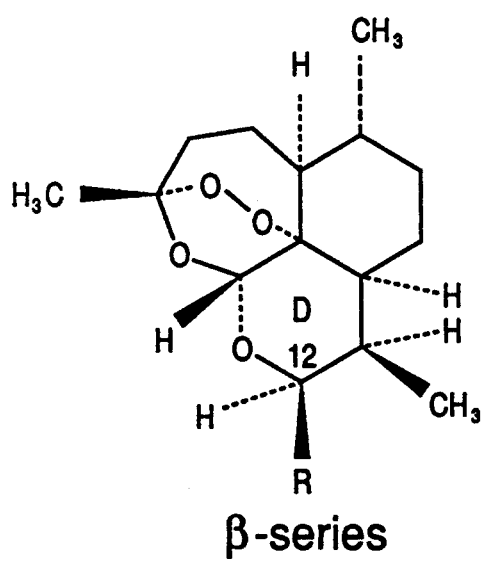

FIG. 2 provides representations of the structures of dihydroqinghaosu (formula II) and its ethyl ether derivative (formula III) both in the $\beta$-form.

Figure 3:
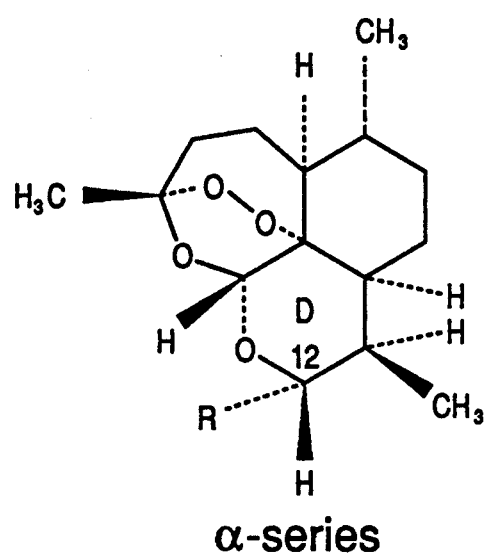

FIG. 3 provides representations of the structures of dihydroqinghaosu (formula II) and its ethyl ether derivative (formula IV) both in the $\alpha$-form.

According to one aspect of the present invention, a process for conversion of the $\alpha$-epimer of arteether to the $\beta$-epimer comprises subjecting the $\alpha$-epimer to an acid catalysed isomerization reaction.

Suitable acid catalysts are boron trifluoride etherate, p-toluene sulphonic acid and hydrochloric acid, as well as other Lewis and Broensted acids, such as boron tribromide, hydrobromic acid and trifluoroacetic acid. The molar ratio of $\alpha$-epimer to catalyst is preferably in the range 0.05 to 0.2. The preferred solvent for performing the acid catalyzed isomerization consists of ethanol or a mixture of ethanol with an aprotic solvent such as benzene, toluene, pentane, hexane and cyclohexane, preferably in the ratio 1 part ethanol to 1-5 parts aprotic solvent. If the solvents comprise cyclohexane and ethanol, they may be present in the ratio 3:1. The preferred temperature is in the range between 50° and 80° C., and the reaction time is suitably between 2 and 4 hours, for example 64° C. for 3 hours.

The $\beta$-isomer is isolated from the reaction mixture by crystallization from an apolar solvent such as a straight chain or branched chain or cyclic alkane with 5 to 7 carbon atoms. Suitable solvents include petroleum ether, pentane, iso-pentane, iso-hexane, cyclohexane, heptane, iso-heptane and particularly hexane.

We have found that yields in excess of 70% of arteether from the $\alpha$-epimer may be achieved by the process of this aspect of the invention.

According to a further aspect of the invention, a modification of the process as hereinbefore described, the modified process being for the synthesis of arteether from artemisininelactol, comprises the reaction of artemisininelactol in a solvent with acid catalyst, the reaction system including an etherifying ethyl moiety, and isolation of the product.

The processes for the conversion of the $\alpha$-epimer of arteether to the $\beta$-epimer and the synthesis of arteether from artemisininelactol are mechanistically very similar and are believed to proceed via a common oxoniumion [$^+$O=C(12)] as intermediate species which yields $\alpha$- and/or $\beta$-ethyletherartemisininelactol, according to which process is being carried out, preferably on reaction with ethanol.

Preferably the reaction temperature is in the range 20° C. to the boiling point of the solvent and the reaction is carried out for about one hour, preferably under reflux. The acid catalyst may comprise hydrochloric acid, p-toluenesulphonic acid or other acid but is preferably a Lewis acid catalyst, such as aluminum chloride or, ideally, boron trifluoride ethyl etherate, which may constitute the etherifying ethyl moiety. The solvent may comprise ethanol, for example a mixture of ethanol and an aprotic solvent such as benzene, toluene, pentane, hexane or preferably cyclohexane, or may comprise another solvent suitable for Lewis acid-catalysed etherification, such as dichloromethane.

The semi-solid crude reaction product comprises arteether as a mixture with its $\alpha$-epimer (IV), which is an oily derivative. Separation of the epimers may be by crystallization from hexane. Concentration of the filtrate may yield further arteether product. Filtration and chromatography of the combined mother liquors may yield additional product and also the $\alpha$-epimer. The mixture of epimers may be subject to the process according to the first aspect of the invention, in order to provide pure arteether in higher yield.

This aspect of the invention permits yields of up to about 70% to be achieved on a scale of several hundred grams.

The dihydroqinghaosu or artemisininelactol starting material may be prepared from qinghaosu by reduction with excess sodium borohydride in methanol. The reaction is preferably carried out at temperatures below room temperature, for example in the range 0°-5° C., since this increases the yield of DQHS product. The crude product is preferably purified by dissolution and recovery from a single solvent, preferably dichloromethane. Yields of approximately 90% may be obtained on a batch size of several hundred grams.

The arteether end product may be characterised by its melting point (80°-82° C.) and optical rotation (+153°-155°) and established as benzene-free by HPLC.

Arteether prepared according to the process of the invention may be formulated as solutions for intra-muscular injection by dissolution in oils such as peanut oil, olive oil, sesame oil, tea seed oil and the like, or as tablets for oral administration as such or in combination with other antimalarial compounds, optionally in unit dosage form.

The process of the present invention will now be described by way of example.

EXAMPLE 1

(i) Dihydroqinghaosu (II)

To a stirred solution of 240 g (0.85 mol) of qinghaosu (I) in 12 l MeOH was added 240 g (6.34 mol) $NaBH_4$ over a period of 1.75 h, keeping the reaction mixture at 0°-5° C. After an additional stirring for 1.25 h under the same conditions, the mixture was neutralized with 375 ml AcOH maintaining the temperature in the 0°-5° C. range, concentrated by distilling off 8.5 l of solvent (45° C./400 mm), and diluted with 7.5 l cold $H_2O$—MeOH (2:1, 0°-5° C.). The filtrate was stored for 14 h at 4° C. The small amount of precipitate formed was collected and washed with 2×30 ml $H_2O$—MeOH (2:1, 0°-5° C.). The wet crops were pooled and dissolved in 7 l $CH_2Cl_2$. After drying (120 g $MgSO_4$) and evaporation of the solvent, 191.4 g (79%) of (II) was obtained: mp 149°-153° C.

(ii) Arteether (III)

A solution of 191 g (0.67 mol) of (II) in 750 ml EtOH and 2.25 l benzene was heated to 45° C. After rapid addition of 9 ml (0.071 mol) $BF_3Et_2O$ the mixture was refluxed for 1 h under $N_2$, washed with 2.4 l saturated NaOAc and 2.25 l $H_2O$, dried (75 g $MgSO_4$) and concentrated to give 210.1 g of a semi-solid mixture of (III) and (IV) (3:1) which was dissolved in 135 ml hexane at 45° C. and stored at −20° C. for 36 h. The white crystalline precipitate was collected, washed with 2×70 ml hexane (<0° C.) and dried to give 136.9 g (65%) of (III): mp 80°-82° C. From the concentrated filtrate a further 14.9 g (7%) of material was obtained: mp 79°-81° C. Total yield of (III): 151.8 g (72%). Recrystallization of this material, together with 351.4 g of (III) of the same quality from another batch, from 330 ml hexane (<0° C., 24 h) afforded, after washing with 250 ml hexane (<0° C.), 456.9 g of (III): mp 80°-82° C. Concentration of the filtrate afforded an additional 36.6 g of material: mp 80°-82° C. The 2 crops were combined and dried (30° C./0.2 mm) to give 493.5 g of pure arteether (III): mp 80°-82° C.; $[\alpha]_D^{21} = +154.5°$ (c 1.0, $CHCl_3$); IR (KBr) 2980, 2960, 2880, 2855, 1451, 1378, 1033, 985, 874; H-$^1$H-NMR($CDCl_3$): 0.91 (d, J=7.5, 3H), 0.96 (d, J=6, 3H), 1.20 (t, J=7.5, $OCH_2CH_3$), 1.45 (s, 3H, 1.10-2.15 (m, 10H), 3.48 and 3.88 (m, $OCH_2CH_3$), 4.83 (D, J=3.5, 1H), 5.43 (s,1H); MS 313 (MH+). Anal. ($C_{18}H_{28}O_5$) C, H, within 0.05%.

(iii) α-Dihydroqinghaosu-ethylether (IV)

Portionwise chromatography of the combined residues (185 g) recovered from all available mother liquors on a 20-fold amount of silica gel in hexane-EtOAc (9:1) lead to an additional 40 g of (III) and 126.9 g of (IV) contaminated with a trace of (III). A sample was rechromatographed to give pure (IV): $[\alpha]_D^{21} = -2.8°$ (c 1.0, $CHCl_3$); IR(CHCl) 2930, 2880, 1380, 1050, 1016, 877; $^1$H-NMR ($CDCl_3$) 0.89 (d, J=7.5, 3H), 0.95 (d, J=6, 3H), 1.21 (t, J=7.5, $OCH_2CH_3$), 1.44 (s, 3H), 1.10-2.20 (m, 10H), 2.20-2.50 (m, 2H), 3.51 and 4.01 (m, $OCH_2CH_3$), 4.45 (d, J=10, 1H), 5.35 (s, 1H); MS 313 (MH+).

(iv) Epimerization of (IV) into (III)

To a solution of 5.13 g (16.4 mmol) (IV) in 60 ml benzene and 20 ml EtOH was rapidly added 240 μl (1.9 mmol) $BF_3Et_2O$ and the mixture was refluxed under $N_2$ for 3 h, washed with 65 ml saturated NaOAc and 60 ml $H_2O$, dried ($MgSO_4$) and concentrated to give 5.01 g (III) and (IV) (2:1). Crystallisation from 3 ml hexane afforded 1.66 g (32%) of (III); mp 79°-80° C. The filtrate was concentrated and the residue chromatographed on 200 g silica gel in hexane-EtOAc(9:1) to yield a further 1.28 g (25%) (III) and 1.48 g (29%) (IV).

EXAMPLE 2

(i) Dihydroqinghaosu (II)

To a stirred solution of qinghaosu (I) (240 g, 0.85 mol) in 12 l MeOH was added $NaBH_4$ (240 g, 6.34 mol) over a period of 2 h keeping the reaction mixture at 0°-5° C. After an additional stirring for 1.30 h under the same conditions, the mixture was neutralized with 375 ml AcOH maintaining the temperature in the range of 0°-5° C. and subsequently diluted with 24 l water. After stirring for 1 h at 0°-1° C., the white precipitate formed was collected and washed with 700 ml water-MeOH (2:1, 0°-5° C.) The filtrate was stirred for 14 h at 0° C. The small amount of material precipitated was collected and washed with $H_2O$—MeOH (2:1, 2×30 ml). The wet crops were combined and dissolved in 7 l $CH_2Cl_2$. After drying on magnesium sulphate (120 g) and evaporation of the solvent, 212 g (88%) of (II) was obtained: mp 149°-153° C.

(ii) Arteether (III)

A solution of (II) (212 g, 0.73 mol) in 810 ml EtOH and 2.43 l cyclohexane was heated to 45° C. After rapid addition of 9.7 ml $BF_3Et_2O$, the mixture was refluxed for 1 h under a $N_2$-atmosphere, washed with 2.6 l saturated NaOAc and 2.45 l water. Each of the aqueous phases was extracted with 100 ml cyclohexane. The combined organic layers were dried with $MgSO_4$ (81 g) and concentrated to give 230.9 g of a semi-solid mixture of (III) and (IV) (3:1) which was dissolved in 146 ml hexane at 45° C. and stored at −20° C. for at least 36 h. The white crystalline precipitate was filtered off, washed with hexane (2×75 ml, <0° C.) and dried to give 144.9 g (63.9%) of (III): mp 80°-82° C. The residue obtained from the mother liquor was crystallized from 40 ml hexane providing an additional 16.9 g (7%) of (III): mp 79°-81° C. The total yield of (III) was 157.3 g (70%).

EXAMPLE 3

(i) Preparation of Dihydroqinghaosu (DQHS) (II)

To a solution of 4 g (0.014 m) of qinghaosu (I) in 200 ml of methanol, was added 4 g of sodium borohydride in small portions, keeping the reaction mixture at 0°-5°.

After stirring for 60 min, the mixture was neutralized with glacial acetic acid, concentrated and diluted with water. The white precipitate formed was collected and dried. Recrystallization of the solid from acetone-hexane afforded white needles mp: 153°-58° C., 3.2 g (80).

(ii) Preparation of Arteether (III) and α-Anomer (IV)

To a solution of dihydroqinghaosu (II) (3.5 g, 0.012 m) in ethanol (15 ml) and dry benzene (30 ml) was added BF$_3$Et$_2$O (15 drops), and the mixture heated to 70° C. for 5 h, washed with saturated NaOAc and H$_2$O, dried with anhydrous Na$_2$SO$_4$, and concentrated to give an oil (3.86 g), which was purified by flash column chromatography on silica gel with petroleum ether (35°-60°)/AcOEt (9:1). Concentration of the first fractions gave arteether (III) as a white solid, which was recrystallized from petroleum ether (35°-60°) to give an analytical sample (2.5 g; 65%) mp 80°-81° C. TLC showed a single spot on silica gel GF plates with the solvent system petroleum ether (35°-60°)/ethyl acetate (9:1) Rf value=0.74 (detection with iodine). $[\alpha]_D^{27.5} = +153.62°$ (c=1.02, CHCl$_3$). IR (CHCl$_3$): 2975 s; 2950 s; 2880 m, 1020 s, 875 m (peroxide). $^1$H-NMR (CDCl$_3$): 3.43-4.03 (m, 2H, O-CH$_2$-CH$_3$), 4.7) (d, 1H, J=3.7 Hz, H-C(12)), 5.41 (s, 1H̄, H-C(5)); MS (CI;NH$_3$): 313 (M$^+$+10. Anal. Calc. for C$_{17}$H$_{28}$O$_5$: C 65.35, H 9.03; found: C 65,44, H 9.05.

(iii) The later fractions obtained were combined and evaporated to give α-anomer (IV) as an oil (750 mg; 19.1%). TLC showed a single spot on silica gel GF plates with the solvent system petroleium ether (35°-60°) ethylacetate (9:1), Rf value=0.61 (detection with iodine). $[\alpha]_D^{27.5} = -2.97$ (c=1.01, CHCl$_3$): 3.45-4.03 (m, 2H, O-CH$_2$-CH$_3$), 4.43 (1, 1H, J=9.3 Hz, H-C(12)), 5.34 (s, 1H̄.H-C(5)). MS (CI; NH$_3$): 313 (M$^+$+1).

EXAMPLE 4

(i) In another epimerization of alpha-isomer IV, a stirred solution of a 6:1 mixture of IV and III (100 g, 0.32 Mol, obtained from the mother liquor of Example 2) in 1.08 l cyclohexane and 360 ml ethanol was heated to 50° C., treated with BF$_3$Et$_2$O (4.3 ml, 0.034 Mol) and refluxed for 3 h under a nitrogen atmosphere. After addition of 1.15 l sat. NaOAc solution, the stirred mixture was cooled with water to room temperature. The two layers were separated and the aqueous layer was extracted once with 100 ml cyclohexane. The combined organic layers were washed with 1.08 l distilled water, dried on 42 g MgSO$_4$ and evaporated to give after drying (30° C./1 torr) an oily residue (99.0 g) consisting mainly of a 2:1 mixture of III and IV.

(ii) Crystallization of III from the epimerization mixture. 377.9 g of a 2:1 mixture of III and IV was dissolved in 210 ml hexane and stored for 60 h at −20° C. The crystalline precipitate was collected, washed with hexane (2×70 ml, 0° C.) and dried to yield 156.8 g (36.1%) of III, m.p. 79°-81° C. The residue (169 g) recovered from the mother liquor and washings was dissolved in 80 ml hexane and stored for 120 h at −20° C. The precipitate was washed with hexane (2×25 ml, 0° C.) and dried, affording 14.0 g (3.2%) of III. The total yield of III was 170.8 g (39.3%).

The oily residue (204.6 g) obtained from the mother liquor and washings was fractionated on a 20 fold amount of silica gel using hexane-EtOAc 9:1 as eluent to yield 50.7 g (13.4%) of III and 105.4 g (27.8%) of IV. The obtained IV was again epimerized according to the procedure described under step (i).

The overall yield of III from I in Examples 2 and 4 run as an overall process according to the invention was 82%.

We claim:

1. A process for conversion of the α-epimer of arteether to the β-epimer, the process comprising subjecting the α-epimer to an acid catalysed isomerization reaction.

2. A process according to claim 1, in which the isomerization reaction is catalysed by boron trifluoride etherate, p-toluene sulphonic acid, hydrochloric acid, boron tribromide, hydrobromic acid or trifluoroacetic acid.

3. A process according to claim 1 or claim 2, in which the molar ratio of α-epimer to catalyst is in the range 0.05 to 0.2.

4. A process according to claim 1, in which the reaction is carried out in a solvent which comprises ethanol or a mixture of ethanol with an aprotic solvent.

5. A process according to claim 1, in which the reaction is carried out at a temperature in the range 50°-80° C.

6. A process according to claim 1, in which the β-epimer is isolated from the reaction mixture by crystallization from an apolar solvent.

* * * * *